United States Patent [19]

Kuo

[11] Patent Number: 4,790,336

[45] Date of Patent: Dec. 13, 1988

[54] DENTAL FLOSS APPLICATOR

[76] Inventor: Ming-Chuan Kuo, 19350 Christina Ct., Cerritos, Calif. 90701

[21] Appl. No.: 76,770

[22] Filed: Jul. 23, 1987

[51] Int. Cl.$^4$ ............................................. A61C 15/00
[52] U.S. Cl. ...................................... 132/325; 132/323
[58] Field of Search .............. 132/89, 91, 92 R, 92 A; D28/64

[56] References Cited

U.S. PATENT DOCUMENTS

| | | | |
|---|---|---|---|
| 3,592,203 | 7/1971 | Johnson | 132/91 |
| 3,881,502 | 5/1975 | Bennington | 132/91 |
| 3,908,677 | 9/1975 | Beach | 132/92 R |
| 4,008,728 | 2/1977 | Sanchez | 132/92 R |
| 4,151,851 | 5/1979 | Bragg | 132/91 |
| 4,178,947 | 12/1979 | McCourry et al. | 132/92 R |
| 4,508,125 | 4/1985 | Loubier | 132/92 R |
| 4,518,000 | 5/1985 | Leverette | 132/92 A |

FOREIGN PATENT DOCUMENTS 2141935  1/1985  United Kingdom ............. 132/92 A

Primary Examiner—John Weiss
Attorney, Agent, or Firm—Christie, Parker & Hale

[57] ABSTRACT

A dental floss applicator comprises a fork having a pair of elongated legs projecting from an elongated handle, a container on the handle for storing a supply of dental floss, and a reel on one side of the handle for being rotated to withdraw a continuous string of dental floss under tension from the container and pass the dental floss from the container along the length of one leg, across the distance between the tips of the legs, after which the floss extends along the length of the other leg and is then wound on a rotatable post on the underside of the handle. The reel and post rotate in unison so that as they rotate, the dental floss is continuously fed from the container across the distance between the tips of the legs where the floss is held under tension for use in teeth cleaning. The relative diameter of the post and reel provide a differential tensioning arrangement for applying a controlled tension to the dental floss across the distance between the tips of the legs. Further controlled tension can be applied to the floss by a movable clip for engaging a stop over which the dental floss passes before being wound on the reel.

25 Claims, 2 Drawing Sheets

DENTAL FLOSS APPLICATOR

FIELD OF THE INVENTION

This invention relates to a dental floss applicator, and more particularly to a floss applicator which makes use of dental floss easier and more effective while minimizing waste and saving time when using dental floss.

BACKGROUND OF THE INVENTION

Dentists cannot overemphasize the importance of regularly using dental floss to clean the areas between the teeth. Dental floss holders have been developed in the past to make regular flossing easier and more effective. One prior art dental floss holder is sold by John O. Butler Co. under the trademark FlossMate. This device is shaped as a fork with an elongated handle and two semi-rigid, narrow elongated and somewhat downwardly curved legs extending in front of the handle. A piece of dental floss is held by the dental floss holder by wrapping one end of the floss around a post on the handle and then extending the floss over one leg, spanning the distance between the ends of the legs, then extending it back along the other leg, and wrapping it around the post. The portion of the dental floss piece which spans the ends of the legs is held somewhat in tension, and this portion of the floss is used for cleaning the spaces between the teeth. The present invention is based on a recognition of several disadvantages of this prior art dental floss holder. For instance, the portion of the floss held between the legs of the holder can become loose during use. If the ends of the floss break off, or if the floss becomes frayed, it takes additional time to sever an additional length of floss and rewind it on the post and around the ends of the fork. In addition, a substantial amount of dental floss is wasted by the unused length of floss which extends along both sides of the fork and around the post in order to hold the floss on the holder.

The present invention provides a dental floss applicator which overcomes these problems.

SUMMARY OF THE INVENTION

Briefly, the dental floss applicator of this invention which includes a fork having a pair of elongated legs projecting from an elongaed handle, and a container on the handle stores a supply of dental floss. Dispensing means on the handle withdraws a continuous string of dental floss from the container under tension and passes the floss from the container, across the distance between the end portions of the legs of the fork so that floss can be continuously fed from the container and across the distance between the legs where it is held under tension for use in teeth cleaning. The dental floss applicator avoids the problem of continuously cutting off lengths of floss and stringing them onto a dental floss holder. Moreover, since floss is continuously fed from the container across the ends of the fork, waste of dental floss is avoided. Further, the dispensing means are arranged to hold the dental floss between the ends of the fork under a controlled amount of tension, which makes flossing easier and more effective.

These and other aspects of the invention are more fully understood by referring to the following detailed description and the accompanying drawings.

DETAILED DESCRIPTION

Figure 1:
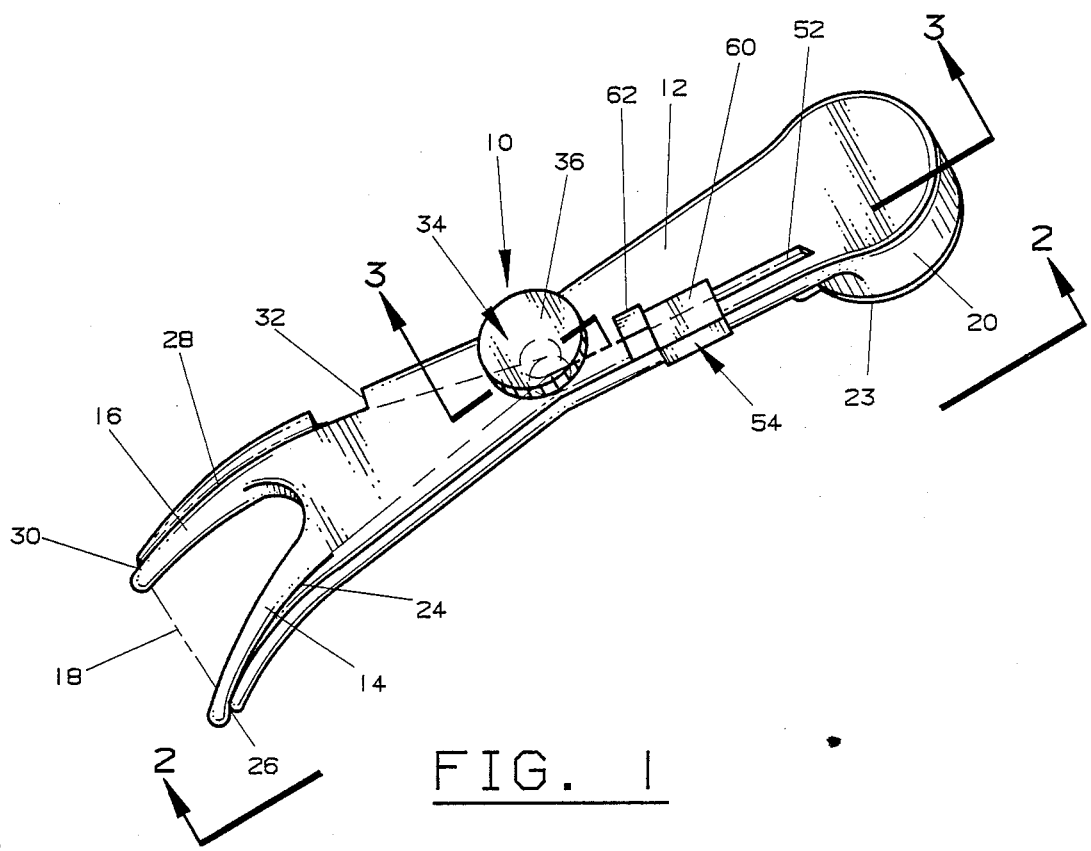
FIG. 1 is a perspective view illustrating a dental floss applicator according to principles of this invention.
Figure 2:
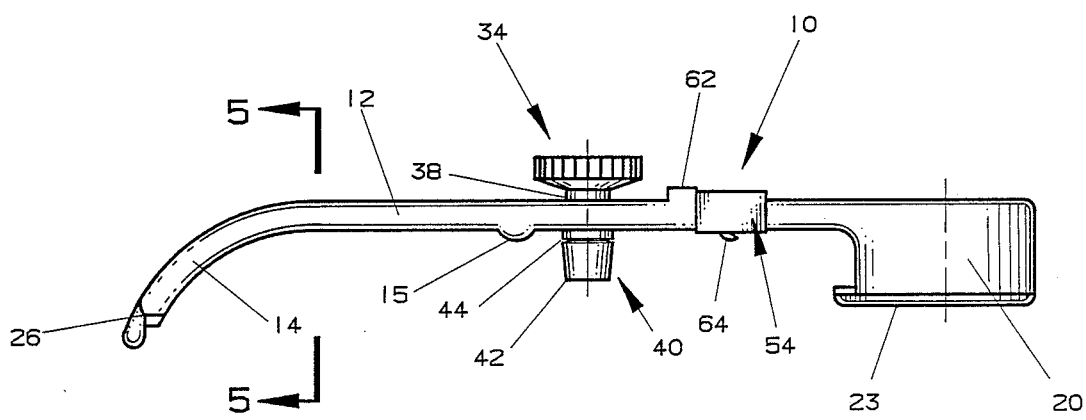
FIG. 2 is a side elevation taken on line 2—2 of FIG. 1.

Referring to FIGS. 1 and 2, a dental floss applicator 10 includes a fork having an elongated handle 12 which is bifurcated at one end to form a pair of spaced apart outwardly projecting, narrow, elongated and somewhat downwardly curved left and right legs 14 and 16, respectively. The handle is preferably made from a hard plastic material so that the legs 14 and 16 are rigid in the sense that they can be held in a fixed spaced apart position to hold a length of dental floss 18 extending between them under tension. However, the legs of the fork are movable somewhat under external pressure so that they can be moved toward one another to shorten the distance between them, but the legs will normally to recover to fixed spacing inherently provided by the molded plastic material.

The handle portion of the fork includes a dental floss container 20 at the end of the fork opposite from the legs 14 and 16. This container is preferably circular in shape and has a hollow interior 21 for containing a supply reel of dental floss 22 shown schematically in FIG. 3. A continuous string of dental floss is unwound from the supply in the container 20 and is passed along the length of the left leg 14 of the fork, and then across the distance between the ends of the fork, passing along the length of the right leg 16 of the fork and then to the underside of the device where the used dental floss is taken up and can be cut off is desired. This means for dispensing the dental floss from the container to the distance between the ends of the fork will be described in greater detail below. At this point it suffices to say that the left leg 14 of the fork has an elongated floss-guiding groove 24 extending along its top surface to a grooved shoulder 26 at the tip of the left leg 14. Similarly, the right leg 16 of the fork has a narrow elongated floss-guiding groove 28 which extends along its upper surface away from a grooved shoulder 30 at the tip of the right leg 16. The dental floss withdrawn from the container 20 is lodged in the groove 24 and passes through that groove, around the shoulder 26, across the space between the tips of the legs, around the shoulder 30, and then along the groove 28 on the top side of the right fork 16. A notch 32 is formed in the handle at the end of the groove 28 in the right fork 16 so that the dental floss then can pass to the underside of the handle to a take-up post described below.

The dental floss is withdrawn from the supply container and passed along the ends of the fork and across the space between them by first wrapping the floss around a reel 34. This reel is rotatably mounted on an upper side of the handle about midway between the tips of the fork and the end of the container. The reel 34 has a large circular knob 36 spaced above the upper surface of the handle. The underside of the knob tapers narrower toward the handle to form a narrow cylindrical shank 38 adjacent the upper surface of the handle. As shown best in FIG. 3, a take-up post 40 on the underside of the handle rotates in unison with rotation of the reel 34. The take-up post includes a tapered stud 42 with a wedge-type groove 44 spaced parallel to and a short distance from the underside of the handle. The take-up stud is rotatably connected to the underside of the reel 34 by a rigid cross-member 46 extending from the take-up stud through a hole in the handle and into a splined hole in the cylindrical base portion of the reel. Thus, rotation of the reel 34 by manually turning the knob 36 also results in rotation of the take-up post 40 on the opposite side of the fork.

Figure 3:
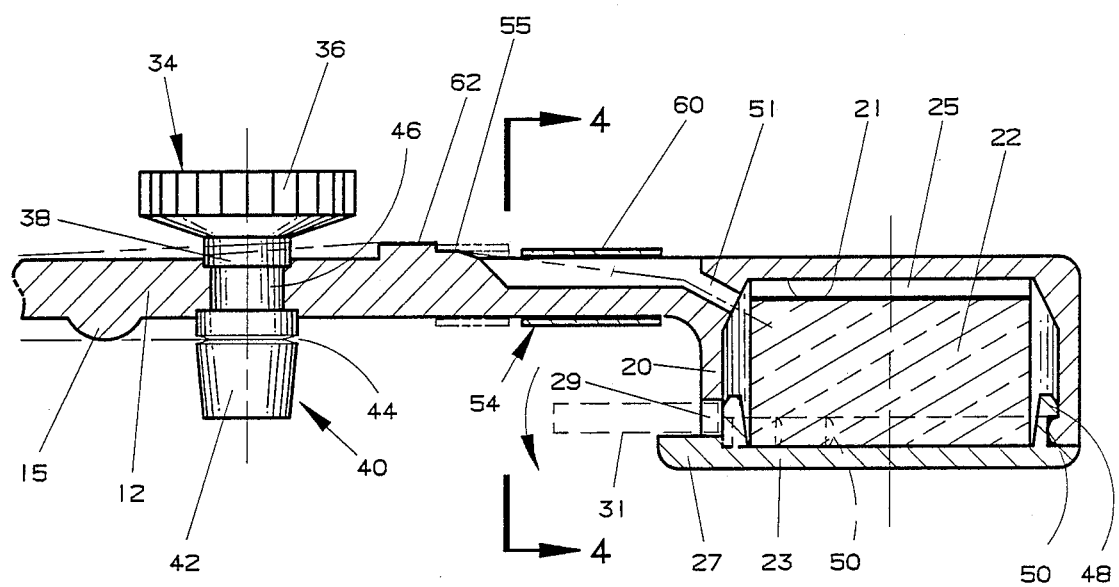
FIG. 3 is a cross-sectional view taken on line 3—3 of FIG. 1.

The supply reel 22 of dental floss is contained in the housing 20 by a snap-on cap 23. A sponge pad 25 is placed between the floss reel 22 and the inside of the housing to prevent vibration of the floss reel. A tongue 27 protrudes from the cap 23 on the side toward the take-up post 40 and is partially engaged in a slot 29 on the housing. The cap 23 can be easily opened by inserting a coin 31 in the slot 29 and prying downward against the tongue 27 as shown in FIG. 3. The cap makes a snap-lock by an annular ring 48 which makes a snap-lock with three equally spaced apart segments of cooperating annular shoulders 50, although other means for releasably fastening a cap to the housing can be used without departing from the scope of the invention. A narrow passage 51 leads from an upper interior portion of the container to a short straight floss groove 52 extending along the upper surface of the handle from the container housing toward the reel 34. The supply reel 22 of dental floss can include an elongated rigid pin 53 to provide a means for initially threading the floss through the passage 51.

Figure 4:
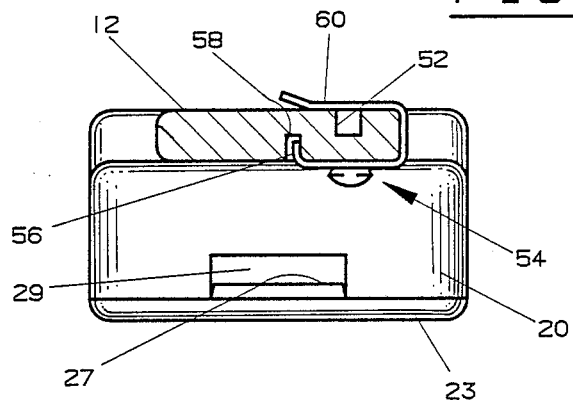
FIG. 4 is a cross-sectional view taken on line 4—4 of FIG. 3.
Figure 7:
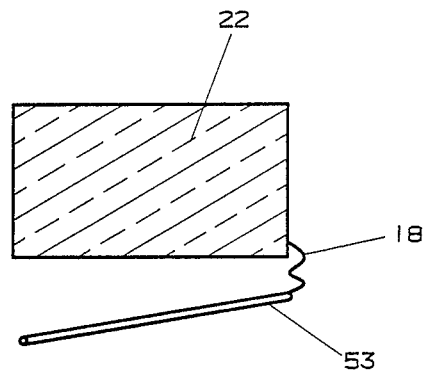
FIG. 7 is a semi-schematic representation of a supply of dental floss with means for feeding the dental floss to the dental floss holder.
Figure 6:
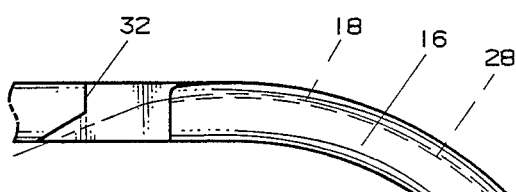
FIG. 6 is a fragmentary elevation view taken on line 6—6 of FIG. 5.
Figure 5:
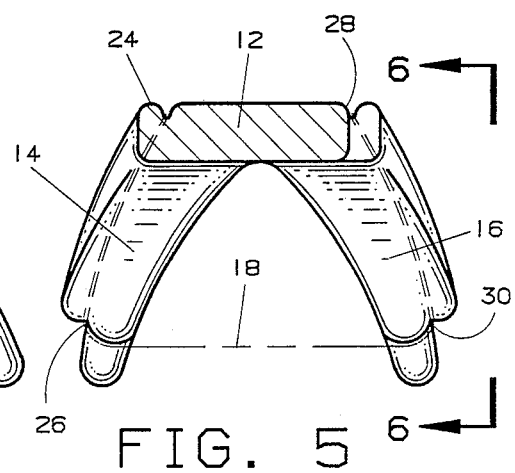
FIG. 5 is a cross-sectional view taken on line 5—5 of FIG. 2.

A floss clip 54 is slidably mounted on a portion of the handle over the floss groove 52 between the container housing and the reel 34. The floss clip is preferably a metal piece bent into a generally U-shaped configuration shown best in FIG. 4. The lower marginal edge 56 of the floss clip is bent upwardly and slides in a straight slot 58 in the underside of the handle. A straight upper portion 60 of the clip slides along the upper surface of the handle 12 above the floss groove 52. At the leading edge of the floss clip 54 an upwardly projecting shoulder 62 projects upwardly away from the upper surface of the handle. The clip is slidable along the length of the handle so that the upper portion 60 of the clip can move toward or away from the shoulder 62. As illustrated in FIG. 1, the clip can be pushed forward so as to engage the leading edge of the shoulder 62 which acts as a stop against further travel of the clip. The travel of the clip in the opposite direction is restrained by engagement of the clip with the end of the slot 58 which terminates near the front side of the container housing 20. Under the clip 54 the upper face of the handle 12 is tapered slightly, between the shoulder 62 and the end of the groove 52, to form a ramp 55. When the clip 54 slides toward shoulder 62, the ramp 55 causes the clip to pinch progressively harder against the floss. A floss cutter 64 is carried on a lower portion of the clip 54.

In using the floss applicator, the dental floss from the supply reel 22 leads through the hole 51 and into the floss groove 52 and then passes over the shoulder 62 and then wraps one or two turns around the shank portion 38 of the reel 34. The floss then leads to the floss-guiding groove 24 along the left fork 14, around the shoulder 26, and across the space between the ends of the fork. The floss then passes around the shoulder 30 and along the floss-guiding groove 28 on the right fork 16. Finally, the floss passes under the slot 32 and to the undersurface of the handle where is it wrapped around the take-up stud 40. The free end of the floss is first wrapped for two or three turns to fill the wedge groove 44 of the take-up stud. The floss is then secured in place by turning the knob 36 which causes the newly fed floss, guided on leveler 15, to wrap over the floss in the groove 44. Since the shank of the take-up stud is slightly wider in diameter than the shank of the reel, this mechanism creates a differential tensioning effect on the floss, with the aid of the clip 54 pinching the floss against the stop shoulder 62. By manually rotating the knob 36, the neck 38 of the reel 40, and the take-up stud 42 rotate in unison which, in turn, withdraws floss continuously from the housing and passes it in a continuous manner along the left leg of the fork, across the space between the tips of the fork, and along the right leg of the fork, to the take-up stud. Since the floss on the take-up stud wraps around a larger diameter post than the floss wrapped around the neck of the reel, by rotating the reel and stud in unison, a greater length of floss is wrapped around the take-up stud than around the reel. This causes extra friction between the floss and the shank 38 and thereby increases the tension in the floss between the tips of the right and left legs 14 and 16. With proper line tension the portion of the floss across the tips of the legs can be easily placed into the gap between the teeth and can be easily moved back and forth along the tooth gap to clean the areas between teeth. To feed the floss, the clip is simply moved away from the stop and the knob on the reel is turned to feed a further length of floss between the tips of the legs.

What is claimed is:

1. A dental floss applicator comprising:
   a fork having a pair of elongated legs projecting from an elongated handle;
   container means on the handle for storing a supply of dental floss;
   dispensing means on the handle for withdrawing a continuous string of dental floss from the container means under tension and passing the dental floss from the container means across the distance between the end portions of the legs of the fork so the dental floss can be continuously fed from the container means across said distance and held thereacross under tension for use in teeth cleaning;
   in which the dispensing means includes a rotatable reel around which the dental floss is wound so that rotation of the reel withdraws the floss from the container means and passes it along the length of one leg and across said distance between the legs; and
   means on the handle adjustably movable into contact with the continuous string of floss between the reel and the supply means to apply a controlled amount of tension to the floss prior to its being wound on the reel.

2. Apparatus according to claim 1 in which the dispensing means further includes a post on a side of the handle opposite from the reel, and in which the reel and post are rotatable in unison so that dental floss extends across said distance and along the other leg and is then wound on the post to apply tension to the portion of the floss extending across said distance between the legs in response to rotation of the reel and post.

3. Apparatus according to claim 2 in which said tension is applied across said distance by differential tensioning means associated with the reel and post.

4. Apparatus according to claim 3 in which the differential tensioning means provided by a greater diameter on the post than on the reel so that rotation of the post and reel in unison causes more floss to be wound on the post than on the reel to apply said differential tension.

5. Apparatus according to claim 2 including a shoulder projecting from the underside of the handle to provide a leveling means for guiding the floss into engagement with a groove on the post.

6. Apparatus according to claim 1 in which the means for contacting the floss comprises a clip moveable toward a stop over which the floss passes before being wound on the reel so the clip can apply pressure to the floss when the clip is moved toward the stop.

7. Apparatus according to claim 6 in which the clip applies pressure to the floss via a wedging action when the clip is moved toward the stop.

8. Apparatus according to claim 1 in which the free end of the floss includes a pin to assist passing the free end of the floss through an opening in the container.

9. Apparatus according to claim 1 in which the container includes a releasable top which includes a slot for receiving a coin for use in prying the top away from the container.

10. Apparatus according to claim 2, in which the floss is engaged with a wedge-type groove on the post.

11. A dental floss applicator comprising a fork having a pair of elongated legs projecting from an elongated handle, container means on the handle for storing a supply of dental floss, dispensing means on the handle for withdrawing a continuous string of dental floss from the container means under tension and pressing the dental floss from the container means, across the distance between end portions of the legs of the fork, the dispensing means including a rotatable reel around which the floss is wound so that rotation of the reel withdraws the floss from the supply means and passes it toward the legs of the fork, the dispensing means further including controlled differential tensioning means for controlling the tension of the dental floss continuously fed from the container means across said distance between the legs of the fork, and including means on the handle adjustably movable into contact with the continuous string of floss between the reel and supply means to apply a controlled amount of tension to the floss prior to the floss being wound on the reel.

12. Apparatus according to claim 11 in which the dispensing means further includes a post on a side of the handle opposite from the reel, and in which the reel and post are rotatable in unison so that dental floss extends across said distance between the legs and along the length of the other leg and is then wound on the post to apply tension to the portion of the floss extending across said distance between the legs.

13. Apparatus according to claim 12 in which the differential tensioning means are provided by a greater diameter on the post than on the reel so that rotation of the post and reel in unison wraps a greater length of dental floss around the post than the reel to apply said differential tension.

14. Apparatus according to claim 12 including a shoulder projecting from the underside of the handle to provide leveling means for guiding the floss into engagement with a groove on the post.

15. Apparatus according to claim 11 in which the means for contacting the floss comprises a clip movable toward a stop over which the floss passes before being wound on the reel so that movement of the clip toward the stop applies controlled tension to the floss.

16. Apparatus according to claim 15 in which the clip applies pressure to the floss via a wedging action when the clip is moved toward the stop.

17. Apparatus according to claim 11 in which the free end of the floss includes a pin to assist passing the free end of the floss through an opening in the container.

18. Apparatus according to claim 11 in which the container includes a releasable top which includes a slot for receiving a coin for use in prying the top away from the container.

19. Apparatus according to claim 12, in which the floss is engaged with a wedge-type groove on the post.

20. A dental floss applicator comprising a fork having a pair of elongated legs projecting from an elongated handle, container means on the handle for storing a supply of dental floss, dispensing means on the handle for withdrawing a continuous string of dental floss from the container means under tension and passing the dental floss from the container means across the distance between end portions of the legs of the fork, the dispensing means including a rotatable reel on one side of the handle and around which the dental floss is wound so that rotation of the reel withdraws the floss from the supply means and passes it along the length of one leg and across said distance between the legs, and dispensing means further including a post on a side of the handle opposite from the reel, and in which the reel and post are rotatable in unison so that dental floss extending across said distance between the legs then passes along the length of the other leg and is wound on the post so that rotation of the reel and post in unison applies tension to the portion of the floss extending across said distance, including means on the handle adjustably movable into contact with the continuous string of floss between the reel and supply means to apply a controlled amount of tension to the floss before the floss is wound on the reel.

21. Apparatus according to claim 20 in which a differential tension is applied to the floss by providing a greater diameter on the post than on the reel so that rotation of the reel and post in unison wraps a greater length of dental floss around the post than the reel to apply said differential tension.

22. Apparatus according to claim 20 including a shoulder projecting from the underside of the handle to provide leveling means for guiding the floss into engagement with a groove on the post.

23. Apparatus according to claim 20 including a clip movable toward a stop over which the floss passes before being wound on the reel, so that movement of the clip toward the stop applied controlled tension to the floss.

24. Apparatus according to claim 23 in which the clip applies pressure to the floss via a wedging action when the clip is moved toward the stop.

25. Apparatus according to claim 20, in which the floss is engaged with a wedge-type groove on the post.

* * * * *

UNITED STATES PATENT AND TRADEMARK OFFICE
CERTIFICATE OF CORRECTION

PATENT NO. : 4,790,336
DATED : December 13, 1988
INVENTOR(S) : Ming-Chuan Kuo

It is certified that error appears in the above-identified patent and that said Letters Patent is hereby corrected as shown below:

On the Front Page:

Abstract, line 15, change "diameter" to -- diameters --.
Abstract, line 20, change "stop over" to -- stopover --.

Column 1, line 19, change "semi-rigid" to -- semirigid --.
Column 1, line 48, change "elongaed" to -- elongated --.
Column 2, line 32, after "normally" delete "to".
Column 2, line 46, before "desired" delete "is" and insert therefor -- if --.

In the Claims:

Column 5, line 18, change "stop over" to -- stopover --.
Column 5, line 39, change "pressing" to -- passing --.
Column 6, line 7, change "stop over" to -- stopover --.
Column 6, line 58, change "stop over" to -- stopover --.

Signed and Sealed this

Twenty-first Day of May, 1991

Attest:

HARRY F. MANBECK, JR.

Attesting Officer

Commissioner of Patents and Trademarks